(12) United States Patent
Dahlqvist et al.

(10) Patent No.: US 10,086,989 B2
(45) Date of Patent: *Oct. 2, 2018

(54) PACKAGING UNIT FOR HYGIENE ARTICLES AND A METHOD OF FORMING A PACKAGING UNIT

(71) Applicant: SCA HYGIENE PRODUCTS AB, Göteborg (SE)

(72) Inventors: Conny Dahlqvist, Göteborg (SE); Ulrika Persson, Göteborg (SE); Sofia Ekstedt, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/318,170

(22) PCT Filed: Jun. 13, 2014

(86) PCT No.: PCT/SE2014/050725
§ 371 (c)(1),
(2) Date: Dec. 12, 2016

(87) PCT Pub. No.: WO2015/190969
PCT Pub. Date: Dec. 17, 2015

(65) Prior Publication Data
US 2017/0151106 A1 Jun. 1, 2017

(51) Int. Cl.
*B65D 65/14* (2006.01)
*B65D 85/07* (2017.01)
(Continued)

(52) U.S. Cl.
CPC .......... *B65D 85/07* (2018.01); *A61F 13/5514* (2013.01); *A61F 13/5515* (2013.01);
(Continued)

(58) Field of Classification Search
CPC ............ A61F 13/58; A61F 2013/55155; A61F 13/55165; B65D 65/15; B31B 19/32
(Continued)

(56) References Cited

U.S. PATENT DOCUMENTS 3,913,580 A 10/1975 Ginocchio
3,957,569 A 5/1976 Freitag
(Continued)

FOREIGN PATENT DOCUMENTS

EP 0 368 914 A1 5/1990
EP 0 841 049 A1 5/1998
(Continued)

OTHER PUBLICATIONS

Office Action (Examination Report No. 1 for Standard Patent Application) dated Feb. 13, 2017, by the Australian Patent Office in corresponding Australian Patent Application No. 2014396900. (3 pages).
(Continued)

*Primary Examiner* — Andrew Perreault
*Assistant Examiner* — Raven Collins
(74) *Attorney, Agent, or Firm* — Buchanan Ingersoll & Rooney PC (57) ABSTRACT

A packaging unit for hygiene articles, the unit being formed from a sheet of material having an inner surface, said inner surface comprising an edge portion being provided with a resealable adhesive for closure of the packaging unit. The sheet has a longitudinal center line and at least one transversely extending folding axis dividing the sheet into a first region and a second region. A tab is arranged at an edge portion of the first region. The tab extends in a longitudinal direction from said edge portion so that an extension of the tab along or parallel to the center line from a tab base to an
(Continued)

outer edge of the tab is 0.5 cm or more. A method of forming the packaging unit is also provided.

16 Claims, 4 Drawing Sheets

(51) Int. Cl.
    *B31B 19/62* (2006.01)
    *B31B 21/00* (2006.01)
    *B65D 75/20* (2006.01)
    *A61F 13/551* (2006.01)

(52) U.S. Cl.
    CPC ........ *A61F 13/55135* (2013.01); *B31B 19/62* (2013.01); *B31B 21/00* (2013.01); *B65D 65/14* (2013.01); *B65D 75/20* (2013.01); *A61F 13/551* (2013.01); *B31B 2219/6007* (2013.01); *B31B 2221/102* (2013.01); *B65D 2575/586* (2013.01)

(58) Field of Classification Search
    USPC ....................................................... 206/438
    See application file for complete search history.

(56) References Cited

U.S. PATENT DOCUMENTS

| | | | |
|---|---|---|---|
| 5,046,608 A * | 9/1991 | Laipply | A47K 10/16 |
| | | | 206/209 |
| 5,167,739 A | 12/1992 | Hutchinson et al. | |
| 5,238,178 A | 8/1993 | Hutchinson et al. | |
| 5,375,764 A | 12/1994 | Sauerwine | |
| H1454 H * | 6/1995 | Cucuzza | 604/385.02 |
| 5,462,166 A | 10/1995 | Minton et al. | |
| 5,567,260 A | 10/1996 | McFall | |
| 5,569,230 A | 10/1996 | Fisher et al. | |
| 5,591,153 A | 1/1997 | Mattingly, III | |
| 5,598,970 A | 2/1997 | Mudry et al. | |
| 5,769,837 A | 6/1998 | Parr | |
| 5,792,131 A | 8/1998 | Mizutani | |
| 5,868,727 A | 2/1999 | Barr et al. | |
| 6,003,760 A | 12/1999 | Abercrombie | |
| 6,015,934 A | 1/2000 | Lee et al. | |
| 6,039,242 A | 3/2000 | Tee | |
| 6,176,850 B1 | 1/2001 | Rosenfeld et al. | |
| 6,186,993 B1 | 2/2001 | Toyoshima et al. | |
| 6,203,512 B1 * | 3/2001 | Farris | A61F 13/47209 |
| | | | 602/57 |
| 6,234,229 B1 | 5/2001 | Tabuchi | |
| 6,322,106 B1 | 11/2001 | Mehta et al. | |
| 7,083,079 B2 | 8/2006 | Bethke | |
| 7,708,727 B2 | 5/2010 | Waltman et al. | |
| 8,231,590 B2 * | 7/2012 | Zander | A47K 10/16 |
| | | | 206/438 |
| 8,900,210 B2 | 12/2014 | Drevik et al. | |
| 2003/0163109 A1 | 8/2003 | Ohba et al. | |
| 2003/0225390 A1 | 12/2003 | Vogt et al. | |
| 2003/0234069 A1 | 12/2003 | Coenen et al. | |
| 2004/0107676 A1 | 6/2004 | Murray | |
| 2005/0137553 A1 | 6/2005 | Bechyne et al. | |
| 2005/0198931 A1 | 9/2005 | Cesiro et al. | |
| 2006/0025739 A1 | 2/2006 | DiPalma et al. | |
| 2006/0137568 A1 | 6/2006 | MacDonald et al. | |
| 2007/0049891 A1 | 3/2007 | Clark, Jr. et al. | |
| 2007/0189644 A1 | 8/2007 | Murray | |
| 2008/0067803 A1 | 3/2008 | Tanigawa | |
| 2009/0082747 A1 | 3/2009 | Carlen et al. | |
| 2010/0078032 A1 * | 4/2010 | Sarros | A61F 6/00 |
| | | | 128/844 |
| 2010/0175825 A1 | 7/2010 | Baldauf | |
| 2010/0298797 A1 | 11/2010 | Ehlenbach et al. | |
| 2011/0028933 A1 | 2/2011 | Fung et al. | |
| 2011/0034897 A1 | 2/2011 | Nomoto et al. | |
| 2012/0090071 A1 | 4/2012 | Umebayashi | |
| 2012/0283682 A1 | 11/2012 | Otsubo et al. | |
| 2013/0165888 A1 | 6/2013 | Kinoshita et al. | |
| 2013/0199956 A1 * | 8/2013 | Hunter | B65D 75/14 |
| | | | 206/459.1 |
| 2014/0155852 A1 | 6/2014 | Nishimura et al. | |
| 2015/0112294 A1 | 4/2015 | Dahl et al. | |

FOREIGN PATENT DOCUMENTS

| | | |
|---|---|---|
| EP | 0 955 243 A2 | 11/1999 |
| EP | 2 589 356 A1 | 5/2013 |
| EP | 2 737 886 A1 | 6/2014 |
| GB | 2 273 279 A | 6/1994 |
| JP | 2003-199786 A | 7/2003 |
| JP | 2006-45417 A | 2/2006 |
| JP | 2009-73498 A | 4/2009 |
| JP | 2013-85818 A | 5/2013 |
| WO | WO 88/10219 A1 | 12/1988 |
| WO | WO 89/00459 A1 | 1/1989 |
| WO | WO 95/00092 A1 | 1/1995 |
| WO | WO 97/34556 | 9/1997 |
| WO | WO 00/45767 A1 | 8/2000 |
| WO | WO 03/030796 A1 | 4/2003 |
| WO | WO 2005/087167 A1 | 9/2005 |
| WO | WO 2010/071512 A1 | 6/2010 |
| WO | WO 2010/135566 A1 | 11/2010 |
| WO | WO 2012/102071 A1 | 8/2012 |
| WO | WO 2012/157621 A1 | 11/2012 |
| WO | WO 2013/162430 A1 | 10/2013 |
| WO | WO 2014/188239 A1 | 11/2014 |

OTHER PUBLICATIONS

Ciba-Geigy AG (Durr's) Applications [1977] RPC 83. Published Feb. 17, 1977.
Section 2.9.2.8 of Australian Patent Manual of Practice & Procedure, titled "Printed Matter". Retrieved Feb. 19, 2017. <http://manuals.ipaustralia.gov.au/patents/national/patentable/2.9.2.8_printed_matter.htm>. (2 pages).
The extended European Search Report dated Oct. 16, 2017, by the European Patent Office in corresponding European Patent Application No. 14894531.4-1308. (7 pages).
English Translation of Office Action (Decision to Grant) dated Jan. 30, 2018, by the Russian Patent Office in Russian Patent Application No. 2017100892/12(001424). (9 pages).
Wikipedia, "Corona treatment", http://en.wikipedia.org/wiki/Corona_treatment, Mar. 16, 2015, 6 pages.
International Search Report (PCT/ISA/210) dated Feb. 23, 2015, by the Swedish Patent Office as the International Searching Authority for International Application No. PCT/SE2014/050724.
Written Opinion (PCT/ISA/237) dated Feb. 23, 2015, by the Swedish Patent Office as the International Searching Authority for International Application No. PCT/SE2014/050724.
International Preliminary Report on Patentability (PCT/IPEA/409) dated Jun. 8, 2016, by the Swedish Patent Office as the International Searching Authority for International Application No. PCT/SE2014/050724.
International Search Report (PCT/ISA/210) dated Feb. 20, 2015, by the Swedish Patent Office as the International Searching Authority for International Application No. PCT/SE2014/050725.
Written Opinion (PCT/ISA/237) dated Feb. 20, 2015, by the Swedish Patent Office as the International Searching Authority for International Application No. PCT/SE2014/050725.
International Preliminary Report on Patentability (PCT/IPEA/409) dated Jun. 13, 2016, by the Swedish Patent Office as the International Searching Authority for International Application No. PCT/SE2014/050725.
International Search Report (PCT/ISA/210) dated Feb. 16, 2015, by the Swedish Patent Office as the International Searching Authority for International Application No. PCT/SE2014/050719.
Written Opinion (PCT/ISA/237) dated Feb. 16, 2015, by the Swedish Patent Office as the International Searching Authority for International Application No. PCT/SE2014/050719.

(56) References Cited

OTHER PUBLICATIONS

International Preliminary Report on Patentability (PCT/IPEA/409) dated Jun. 14, 2016, by the Swedish Patent Office as the International Searching Authority for International Application No. PCT/SE2014/050719.
European Patent Office Letter dated Mar. 27, 2015, for International Application No. PCT/SE2014/050719.
International Search Report (PCT/ISA/210) dated Feb. 11, 2015, by the Swedish Patent Office as the International Searching Authority for International Application No. PCT/SE2014/050720.
Written Opinion (PCT/ISA/237) dated Feb. 11, 2015, by the Swedish Patent Office as the International Searching Authority for International Application No. PCT/SE2014/050720.
Written Opinion of the International Preliminary Examining Authority (PCT/IPEA/408) dated Jun. 3, 2016, by the Swedish Patent Office as the International Searching Authority for International Application No. PCT/SE2014/050720.
Written Opinion of the International Preliminary Examining Authority (PCT/IPEA/408) dated Jul. 7, 2016, by the Swedish Patent Office as the International Searching Authority for International Application No. PCT/SE2014/050720.
European Patent Office Letter dated Aug. 24, 2015, for International Application No. PCT/SE2014/050720.
European Patent Office Letter dated Jun. 29, 2016, for International Application No. PCT/SE2014/050720.
International Search Report (PCT/ISA/210) dated Mar. 2, 2015, by the Swedish Patent Office as the International Searching Authority for International Application No. PCT/SE2014/050726.
Written Opinion (PCT/ISA/237) dated Mar. 2, 2015, by the Swedish Patent Office as the International Searching Authority for International Application No. PCT/SE2014/050726.
Written Opinion of the International Preliminary Examining Authority (PCT/IPEA/408) dated Jun. 3, 2016, by the Swedish Patent Office as the International Searching Authority for International Application No. PCT/SE2014/050726.
International Preliminary Report on Patentability (PCT/IPEA/409) dated Jul. 12, 2016, by the Swedish Patent Office as the International Searching Authority for International Application No. PCT/SE2014/050726.
European Patent Office Letter dated Apr. 7, 2015, for International Application No. PCT/SE2014/050726.
International Search Report (PCT/ISA/210) dated Feb. 11, 2015, by the Swedish Patent Office as the International Searching Authority for International Application No. PCT/SE2014/050718.
International Preliminary Report on Patentability (PCT/IPEA/409) dated Jun. 8, 2016, by the Swedish Patent Office as the International Searching Authority for International Application No. PCT/SE2014/050718.
European Patent Office Letter dated Mar. 27, 2015, for International Application No. PCT/SE2014/050718.

* cited by examiner

PACKAGING UNIT FOR HYGIENE ARTICLES AND A METHOD OF FORMING A PACKAGING UNIT

TECHNICAL FIELD

The present disclosure relates to a packaging unit for hygiene articles. The present disclosure also relates to a method of forming a packaging unit for hygiene articles from a sheet of material.

BACKGROUND

Disposable hygiene articles, such as sanitary napkins and panty liners, are normally packaged individually in, for example, an easy wrap or a single wrap. Individual packages facilitate hygienic carrying of single articles for future use, e.g. in a handbag. The edges of the individual packages can be sealed by means such as ultrasonic welding or heat welding. Further, the packaging units are often used both as a means for packaging an unused article and for disposal of the used article.

It is desirable that used articles of this kind can be disposed of discretely and hygienically. This may be particularly important when the user lacks the possibility to dispose of the used article immediately after the used article has been replaced, e.g. when there is no waste bin available in the toilet area. In this case, the user may need to put the used article in e.g. a handbag or backpack, which requires that the package is adequately sealed in order to avoid staining and odour.

To solve the problem of providing a single wrap that may be both used for packaging of a new and unused hygiene article and for safe and hygienic disposal of used hygiene articles, the use of "post-it-like" adhesives has been shown to be useful as sealing means for the individual wrap packages.

WO2013/162430 A1 discloses such a packaging unit in the form a single wrap that can be used both for packaging of a new and unused hygiene article and for safe and hygienic disposing of used hygiene articles. The packaging unit is in the form of a sheet provided with adhesive in a certain chessboard pattern for closing and sealing the packaging unit. Furthermore, the sheet may be squared-formed and a corner of such sheet is then made adhesive free to form a gripping portion for easier opening.

Although said prior art packaging unit to some extent may alleviate the problems of providing a reliable and hygienic packaging for unused as well as used hygiene articles, there is still a problem of handling the packaging unit, wherein it may be difficult to easily open the package with a new hygiene article and thereafter insert a used hygiene article for disposal and properly reseal the package for disposal.

Thus, there is still a need for further improvements of packaging units so as to provide packaging unit that is easy to handle and reliable in use.

SUMMARY

In view of known packaging units, it is an object of the present disclosure to provide an improved packaging unit arrangement for carrying new hygiene articles as well as used hygiene articles, which arrangement provides easy handling, while being reliable in use.

This object is wholly or partially achieved by a packaging unit according to the present disclosure. Embodiments are set forth in the following description and in the drawings.

Thus, there is provided a packaging unit for hygiene articles, the unit being formed from a sheet of material having a longitudinal direction (L) and a transverse direction (T). The sheet has an inner surface and an outer surface, wherein the inner surface comprises an edge zone that comprises an edge portion being provided with a resealable adhesive for closure of the packaging unit. The sheet has a longitudinal center line (L1) and at least one transversely extending folding axis. The folding axis divides the sheet into a first region and a second region. A sheet-formed tab is arranged at an edge portion of the first region and at least partially along the center line (L1). The tab has two major surfaces being free of any adhesive for closure of the packaging unit. The sheet-formed tab extends in a longitudinal direction from said edge portion so that an extension (A) of the tab along or parallel to the center line (L1) from a tab base (B) to an outer edge of the tab is 0.5 cm or more. The tab base (B) is a transversal line (B) that longitudinally divides the tab with adhesive-free surfaces from a portion of the first region containing said resealable adhesive for closure of the packaging unit, to which resealable adhesive the tab base (B) has a point of contact.

The point of contact is at an edge of a resealable adhesive that provides the shortest extension (A).

The packaging unit is in the form of a sheet that may be used as a single wrap that has resealable adhesive for closure of the packaging unit when holding an unused hygiene article therein or a used article therein.

As used herein, the term "inner surface" refers to the surface of the packaging unit facing the product positioned inside the packaging unit, and the term "outer surface" refers to the surface opposite to the inner surface, i.e. the surface facing the ambient.

By the term "edge zone" is meant the portion of the packaging unit adjacent to the edges of the packaging unit. The width of an edge zone may be varied. The edge zone may be divided into an inner edge portion and an outer edge portion. The term "inner edge portion" then refers to the portion of the edge zone positioned towards the center of the packaging unit, such as towards the longitudinal centerline and transversal centerline of the packaging unit. The term "outer edge portion" refers to the portion of the edge zone positioned towards the edge of the packaging unit.

By a "resealable adhesive" as used herein is meant adhesive that provides that an object may be attached to a surface using such an adhesive and subsequently detached from that surface causing minor or no disruptions of the object and the surface. Furthermore, an object that has been peeled off may also be reattached to a surface again.

The sheet-formed tab forms a gripping tab that provides means to make it easier for the user to grip and open and close the wrap. The gripping tab is easy to grip and localize, in contrast to the known single wraps and pouches, for which it is difficult to localize and see the edge for opening of the wrap.

WO2013/162430 A1 discloses that at least one of the corner portions of a sheet may be free from adhesive such that a gripping tab is formed in order to facilitate opening.

It has now been found that it may be difficult to effect the opening of a closed and folded packaging by the use of such corner tab. Furthermore, the opening by the use of such a corner tab may disrupt the material of the sheet due to uneven load during the opening. In addition, the grip area in the corner does not provide any suitable means for resealing the packaging unit. The user would intuitively try to find any means for opening a packaging in a center portion of a free-end edge of a packaging unit and would normally not even consider the corner for opening of the packaging.

The present packaging unit has a tab that is adhesive-free at the portion protruding outwards from the packaging unit to provide finger-gripping surfaces close to, or at, the center portion of the free-end edge.

The resealable adhesive is provided on edge portions of the sheet such that when the sheet is folded about said at least one folding axis, the resealable adhesive aids in the closure of the packaging unit enclosing a hygiene article.

The sheet-formed tab extension (A) in the longitudinal direction from the edge portion from the tab base (B) to the outer edge is 0.5 cm or more, and may be 1 cm or more, or 2 cm or more. The extension (A) may be up to 3 cm, 4 cm, or 5 cm. Thus, the extension may, for example be 0.5 to 5 cm, 1 to 4 cm or 2 to 3 cm. The width of the tab in the transverse direction (T) depends on the shape of the tab and may be up to a transverse distance between two points of intersection between the tab base (B) and the outer edge (-s) of the packaging unit.

The sheet may be folded along said at least one folding axis with said first and second regions in an overlapping configuration, thereby providing a packaging unit of overlapping sheet layers.

The sheet of material may be of substantially rectangular shape and may comprise longitudinal edges and transverse edge portions, wherein the sheet-formed tab is arranged at one of the transverse edge portions.

As mentioned above, the packaging unit comprises at least one first folding axis. The number of folding axes may vary depending on how the packaging unit is intended to be folded. It is preferred that the packaging unit comprises between one and three folding axes.

The sheet may have two folding axes, dividing said sheet into the first region, the second region and a third region. The sheet may be folded along the folding axes with said first, second and third regions in an overlapping configuration of three layers. The first region may then form an outer layer of the folded packaging unit and the sheet-formed tab may comprise a tab portion that protrudes outwardly from an edge defined by the overlapping sheet layers of the folded packaging unit.

A tab portion that extends from the edge of the folded packaging unit provides a free end and material overhang that is adhesive-free and easy to grip by a user's hand as compared to known adhesive-free end portions and tabs. Such a sheet-formed tab portion does not overlap with any other packaging unit regions.

The longitudinal tab extension (overhang) from the edge, as defined by the overlapping sheet layers of the folded packaging unit, to the outer edge of the tab along or parallel to the center line (L1) may be 0.5 to 5 cm; 1 to 4 cm, or 2 to 3 cm.

In the art it has not been indicated that a tab overhang as described herein could be used and would be beneficial for use in a packaging unit of the present kind. To the contrary, the skilled person would not consider such an overhang due to increased risk of disruption and thus the provision of less reliable packaging units. It has now been found that such an overhang may indeed provide a reliable product when used in combination with resealable adhesive means for closure of the packaging unit as described herein.

The inner surface of the first region may comprise a transverse edge portion of the inner surface that comprises the resealable adhesive for closure of the packaging unit to which the tab base (B) is in contact.

This provides edge fastening by resealable adhesive means, in particular closing means that does not require a tab with adhesive so as to close the packaging. The resealable adhesive at the edge zone portion also keeps the tab secured to the packaging opening in a correct position. It provides reliable closure together with the tab, with minimum risk of undesirable opening of a closed package.

The resealable adhesive may extend in a transverse direction and parallel to the tab base to which the resealable adhesive may have contact.

The tab may have any shape, such as rectangular, triangular and tongue shaped, that is suitable for providing a finger-gripping tab with the dimensions mentioned herein.

The longitudinal extension of the tab may decrease in a transversal direction from the center line (L1). The sheet-formed tab may be tongue-shaped, wherein the tip of the tongue shape is arranged close to, or at, the center line (L1).

By the term "close to" is here meant a transversal distance from the center line (L1) that is within 10% of transversal extension of the sheet.

The maximum extension of the tab from the tab base B to of the tab may be along the center line (L1).

The sheet may a laminate material. By the term "laminate" is meant a material comprising at least two united separable plies of material that can be the same or different. In the context of the present disclosure, the laminate may for example be constituted of two separable plies of plastic film, a film and nonwoven, two plies of nonwoven or the like.

The sheet may be a single-ply material.

By the term "single ply" is meant a packaging unit comprising a single ply of a coherent material. Examples of a single ply packaging unit may be a plastic film, such as a polyethylene film, a nonwoven material, a metallic foil or the like. A single ply material may be a non-homogenous material, such as a plastic film material comprising integrated layers, or a nonwoven material having varying fibre composition in different parts of the material. A single ply material as used herein does not comprise materials having separable layers.

The single-ply material may be of polyolefin that may comprise or be of polyethylene and/or polypropylene. The material of polyethylene and/or polypropylene may have a basis weight of 14 to 30 g/m2.

The tab may be integrally formed with the sheet.

A chessboard pattern of resealable adhesive and non-adhesive portions may be formed along each edge zone of the sheet material for complementary attachment between resealable adhesive and non-adhesive portions in a folded packaging unit.

Examples of different chessboard patterns will be further explored herein below. WO2013/162430 A1 discloses further examples of such patterns.

The sheet and/or tab may be opaque and/or may comprise print and/or tactile indications.

Thus, the tab may be embossed. This provides means for, for example, tactile recognition and a surface that is easier to grip, wherein the friction between the user's hand and the tab is increased.

The print may be in the form of instructions or indications that guide the user in the manipulation of the packaging unit and/or the hygiene article.

The resealable adhesive may be a pressure-sensitive hot-melt adhesive. Such an adhesive provides unlimited open time, meaning that the resealable adhesive can bond to another substrate at any time. Such a resealable adhesive may provide "post-it-like" adhesive properties. Thus, the packaging unit may be reclosable.

Accordingly, the pressure-sensitive adhesive used with the packaging unit is one which has a very high self-adhesion but which can be readily separated or released from other materials, such as plastic materials or paper which has been treated with a release agent. A major advantage of the packaging unit according to the present disclosure is that it can be completely unfolded when a new hygiene article is about to be taken out. In contrast thereto, prior art packages having adhesively sealed edges with adhesive-coated edge portions being in contact with each other have too high adhesive strength of the adhesively sealed edges, and any attempt to completely unfold the package generally leads to tearing and breakage of the packaging unit, making it unusable for discrete and hygienic disposal of the used article. As the adhesive-coated edge portions of the packaging unit of the present disclosure are not in contact with each other when the packaging unit is folded, the packaging unit can be readily opened and resealed, providing a tight disposal package. At the same time, the tensile strength of the adhesively sealed edges of the packaging unit using the adhesive pattern of the present disclosure is sufficient to provide a tight package for both a new and a used article, and low enough to provide a readily-opened package.

The resealable adhesive used in the present disclosure may be a pressure-sensitive hotmelt adhesive, such as Lunatack® D656 BD 19 available from H. B. Fuller.

The length of the resealable adhesive-covered edge portions in each region may be equal to or shorter than length or width of the each region. The width of the adhesive-covered edge portions may be varied depending on the adhesive strength desired. The wider the adhesive-covered edge zones, the stronger the sealing. The width of the resealable adhesive-covered edge portions may be same or different in the different regions.

The sheet of material forming a packaging unit according to the present disclosure may comprise an odour-inhibiting or odour-neutralising substance. Such a substance may be applied in any suitable manner known to the person skilled in the art, e.g. as a coating, activatable microcapsules, impregnated patches, or the like.

It is conceivable that the sheet for forming a packaging unit according to the present disclosure may be stretchable or expandable, which may be advantageous if the hygiene article is greatly deformed during use, and may thus be difficult to wrap without deforming the packaging unit.

It should be noted that when the packaging unit according to the present disclosure is used for disposal, the user may choose to roll up the packaging unit instead of folding, regardless of the adhesive pattern at the edge zone of the packaging unit. This rolling action is made easier by the provision of a finger-gripping tab.

There is also provided a method of forming a packaging unit for hygiene articles. The unit is formed from a sheet of material having a longitudinal direction (L) and a transverse direction (T). The method comprises the steps of:

a. providing the sheet of material, the sheet having an inner surface and an outer surface, said inner surface comprising an edge zone, and b. providing an edge portion of the edge zone with resealable adhesive.

The sheet has a longitudinal center line (L1) and at least one transversely extending folding axis dividing the sheet into a first region and a second region. A sheet-formed tab is arranged at an edge portion of the first region and at least partially along the center line (L1). The tab has two major surfaces being free of any adhesive for closure of the packaging unit. The sheet-formed tab extends in a longitudinal direction from the edge portion so that an extension (A) of the tab along or parallel to the center line (L1) from a tab base (B) to an outer edge of the tab is 0.5 cm or more. The tab base (B) is a transversal line (B) that longitudinally divides the tab with adhesive-free surfaces from a portion of the first region containing the resealable adhesive for closure of the packaging unit, to which resealable adhesive the tab base (B) has a point of contact.

The sheet-formed tab extension (A) in the longitudinal direction from the edge portion from the tab base (B) to the outer edge is 0.5 cm or more, and may be 1 cm or more, or 2 cm or more. The extension (A) may be up to 3 cm, 4 cm, or 5 cm. Thus, the extension may, for example be 0.5 to 5 cm, 1 to 4 cm or 2 to 3 cm.

The method may further comprise the step of folding the sheet along the at least one folding axis with the first and second regions in an overlapping configuration, thereby providing a packaging unit of overlapping sheet layers.

In such a folded packaging unit, the tab may form an overhang having extension dimensions as discussed herein above as described herein above.

The formed packaging unit for hygiene articles may be a packaging unit as described in more detail herein above and in the detailed description.

The present disclosure will now be described in more detail with reference to embodiments and drawings.

DETAILED DESCRIPTION OF EMBODIMENTS

The packaging unit of the present disclosure is in the form of a sheet that may be used as a single wrap that has resealable adhesive for closure of the packaging unit holding an unused hygiene article therein or a used article therein. The closure of the packaging unit may include folding the sheet and enclosing the hygiene article between folded sheet layers that are sealed by the resealable adhesive provided close to the edges of the sheets.

In the following, the packaging unit will be exemplified by a packaging unit comprising a rectangular sheet. Other forms, such as circular sheet, are also within the scope of the appended claims. Furthermore, the exemplified packaging unit comprises resealable adhesive for closure of the packaging unit, wherein a chessboard pattern of resealable adhesive and non-adhesive portions is formed along at least longitudinal edge zones (i.e. along the longitudinal direction (L)) for complementary attachment between resealable adhesive and non-adhesive portions in a folded packaging unit. According to the present disclosure, other ways of applying one or more resealable adhesive portions for closure of the packaging unit may also be considered.

Figure 1:
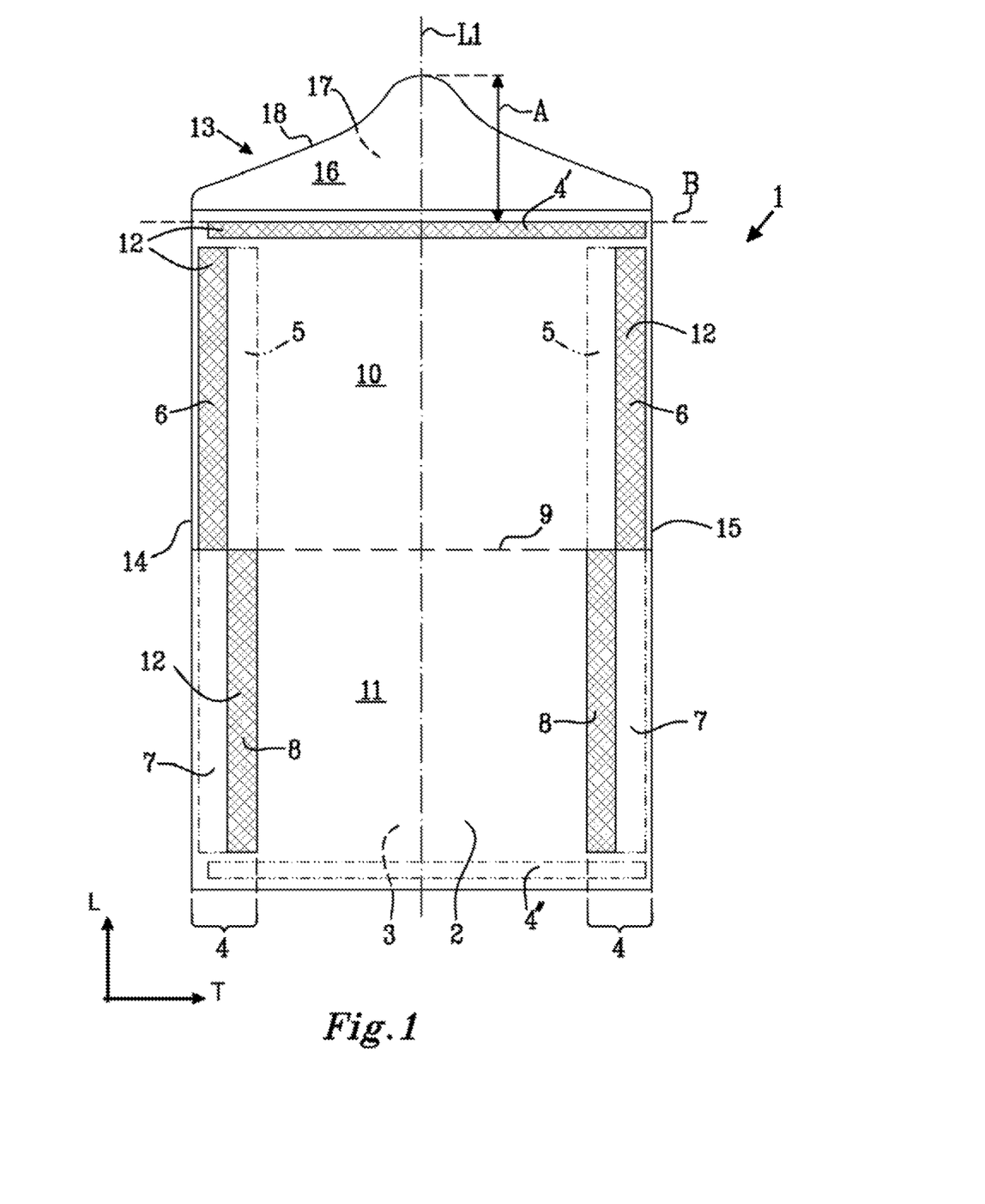
FIG. 1 shows a packaging unit according to an embodiment having one folding axis.
Figure 2:
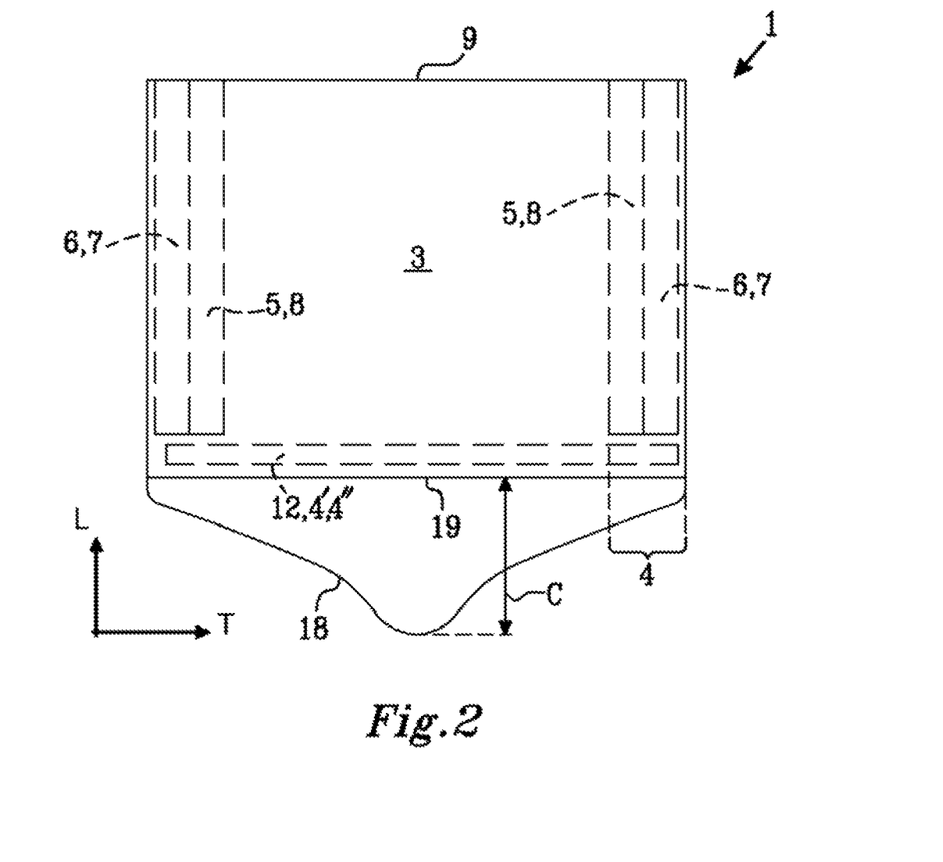
FIG. 2 shows the packaging unit depicted in FIG. 1 in a folded state.

FIG. 1 depicts a packaging unit 1 for hygiene articles according to the present disclosure. The packaging unit is formed from a sheet of material having a longitudinal direction (L) and a transverse direction (T). The sheet has an inner surface 2 and an outer surface 3, the inner surface comprising an edge zone 4 comprising an inner edge portion 5, 8 and an outer edge portion 6, 7. The packaging unit 1 also comprises transverse edge portions 4' and 4". The sheet has a longitudinal center line (L1) and a folding axis 9, wherein the folding axis divides the sheet into a first region 10 and a second region 11. As shown in FIG. 1, the outer edge portion 6 of the edge zone 4 of the first region 10 is provided with resealable adhesive 12, while the inner edge portion 5 of the edge zone 4 of the first region 10 is adhesive-free. Further, the inner edge portion 8 of the edge zone 4 of the second region 11 is provided with resealable adhesive 12, while the outer edge portion 7 of the edge zone 4 of the second region 11 is adhesive-free. Also, the transverse edge portion 4' of the first region 10 is provided with resealable adhesive 12, while the transverse edge portion 4" of the second region 11 is adhesive-free. Thus, the resealable adhesive pattern in the first region 10 is complementary to the resealable adhesive pattern of the second region 11. This in turn means that, when the sheet is folded about the folding axis 9 as shown in FIG. 2, the edge portions 6 carrying resealable adhesive in the first region 10 are brought in contact with the adhesive-free edge portions 7 in the second region 11, the edge portions 8 carrying resealable adhesive 12 in the second region 11 are brought in contact with the adhesive-free edge portions 5 in the first region 10, and the transverse edge portion 4' carrying resealable adhesive 12 in the first region 10 is brought in contact with the adhesive-free transverse edge portion 4" in the second region 11. As can be seen from FIG. 2, the width of the sealing area corresponds to the sum of the widths of the resealable adhesive portions 6, 8. Such a sealing ensures a tight package for both a new and a disposed article.

Furthermore, the packaging unit 1 further comprises a sheet-formed tab 13 arranged at a transverse edge portion of the first region and at least partially along the center line (L1). The illustrated substantially rectangular-shaped sheet comprises longitudinal edges 14, 15 and transverse edge portions 4', 4", wherein the sheet-formed tab 13 is arranged at one (4') of the transverse edge portions. The sheet-formed tab 13 is tongue-shaped, wherein the tip of the tongue shape is arranged close to, or at, the center line (L1). As described above, other shapes may also be considered for providing a finger-gripping tab 13. The tab 13 has two major surfaces 16, 17 being free of any adhesive for closure of the packaging unit. The sheet-formed tab 13 as shown in FIG. 1 extends in a longitudinal direction from the transversal edge portion and has an extension (A) along the center line (L1) from a tab base (B) to an outer edge 18 of the tab (13). The tab base (B) is a transversal line (B) that longitudinally divides the tab 13 with adhesive-free surfaces from the transverse edge portion 4' carrying resealable adhesive 12 in the first region 10, to which resealable adhesive 12 the tab base (B) has a point of contact. The point of contact is at an edge of the resealable adhesive 12 that provides the shortest extension (A).

Thus, the packaging unit 1 has a tab 13 that is adhesive-free at the portion protruding outwards from the packaging unit 1 to provide finger-gripping surfaces close to, or at, a center portion of a free-end edge of the packaging unit. The illustrated sheet-formed tab 13 is easy to grip and localize. It provides means to open and close the packaging unit 1 in the form a wrap. The user would intuitively try the tab means 13 for opening a packaging in the center portion of the free-end edge of the packaging unit.

The sheet-formed tab extension (A) in the longitudinal direction from said edge portion 4' from the tab base (B) to the outer edge 18 is 0.5 cm or more, and may be 1 cm or more, or 2 cm or more. The extension (A) may be up to 3 cm, 4 cm, or 5 cm. Thus, the extension may, for example, be 0.5 to 5 cm, 1 to 4 cm or 2 to 3 cm. The extension (A) may, as illustrated in the drawing, be the maximum longitudinal extension of the tab 13. The width of the tab 13 in the transverse direction (T) depends on the shape of the tab 13 and may be up to a transverse distance between two points of intersection between the tab base (B) and the outer edge (-s) 14,15 of the packaging unit 1.

In FIG. 1, and as described herein above, the resealable adhesive (-s) is provided on edge portions such that when the sheet is folded about the folding axis 9, the resealable adhesive aids in the closure of the packaging unit 1 enclosing a hygiene article. FIG. 2 illustrates a folded sheet along the at least one folding axis, with the first and second regions 10, 12 in an overlapping configuration, thereby providing a packaging unit 1 of overlapping sheet layers.

In the folded packaging unit, the sheet-formed tab 13 protrudes from an edge 19 formed of the overlapping sheet layers. A tab portion extends from the edge 19 of the folded packaging unit and provides a free-end and material overhang that is adhesive-free and easy to grip by a user's hand as compared to known adhesive-free end portions and tabs. The sheet-formed tab 13 portion does not overlap with any other packing unit regions 10; 11. The longitudinal tab extension (C; overhang) from the edge 19 formed by the overlapping sheet of layers to the outer edge 18 of the tab 13 along or parallel to the center line (L1) may be 0.5 to 5 cm; 1 to 4 cm, or 2 to 3 cm.

Figure 3:
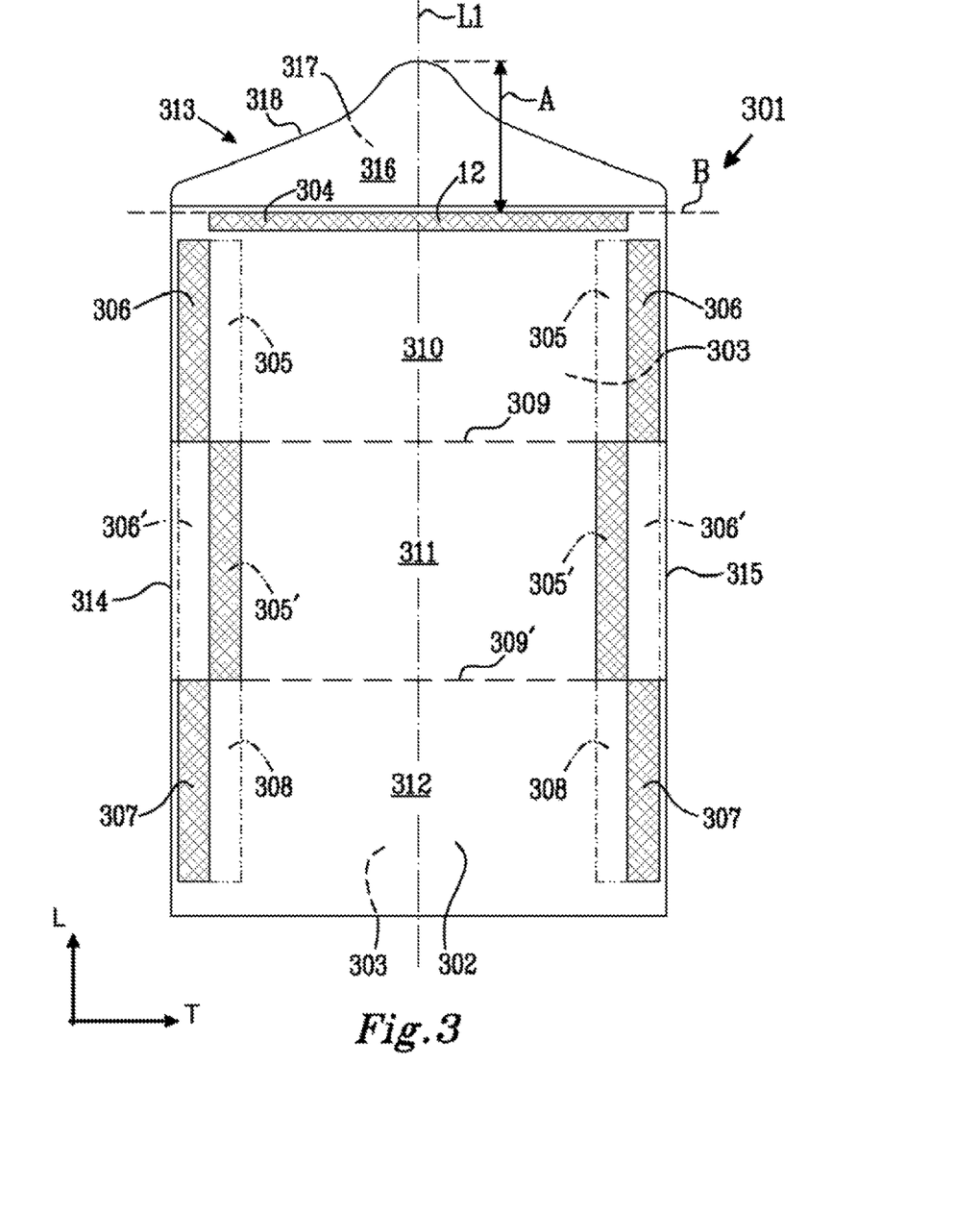
FIG. 3 shows a packaging unit according to an embodiment having two folding axes.
Figure 4:
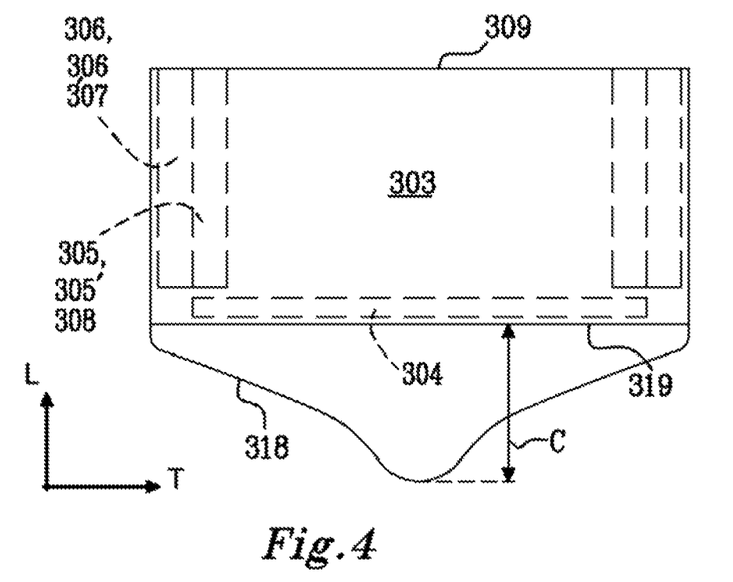
FIG. 4 shows the packaging unit depicted in FIG. 3 in a folded state.

The most common packaging unit for individual packaging of absorbent articles is a rectangular sheet of material having a longitudinal direction (L) and a transverse direction (T) with a longitudinal center line (L1) and which sheet comprises two folding axes, longitudinal edges and transverse edges. Such an embodiment is illustrated in FIG. 3. The packaging unit 301 is a rectangular sheet comprising two folding axes 309, 309' dividing the packaging unit into a first region 310, a second region 311 and a third region 312. Each of the regions comprises an inner edge portion 305, 305', 308 and an outer edge portion 306, 306', 307. As shown in FIG. 3, the outer edge portions 306, 307 of the first and third regions respectively are provided with resealable adhesive 12, while the inner edge portions 305, 308 of the first and third regions respectively are adhesive-free. The resealable adhesive pattern of the second region 311 is complementary to the adhesive pattern of the first and third regions 310, 312, thus forming a chessboard pattern. In other words, the outer edge portion 306' of the second region 311 is adhesive-free, and the inner edge portion 305' of the second region 311 is provided with resealable adhesive. This in turn means that, when the sheet is e-folded about the folding axes 309, 309' as shown in FIG. 4, the outer edge portions 306 of the first region 310 or the outer edge portions 307 of the third region 312 carrying resealable adhesive 12 are brought in contact with the adhesive-free outer edge portions 306' in the second region 311, depending on which of the first and the third regions 310, 312 is brought in contact with the second region 311. Consequently, the inner edge portions 305' carrying resealable adhesive 12 in the second region 311 are brought into contact with the adhesive-free inner edge portions 305 of the first region 310 or the adhesive-free inner edge portions 308 of the third region 312.

As can be seen from FIG. 4, the width of the sealing area corresponds to the sum of the widths of the resealable adhesive portions 306, 305'. The packaging unit may be folded around the second folding axis 309', bringing the third region 312 in contact with the second region 311, sealing the outer edge portions 307, 306' and the inner edge portions 308, 305'. The packaging unit is subsequently folded around the first folding axis 309', bringing the first region 310 in contact with the outer surface of the third region 312, thus sealing the packaging unit (FIG. 4). Thus, the packaging unit will provide a tight and hygienic package.

The packaging unit 301 further comprises a sheet-formed tab 313 that is arranged at the transverse edge portion 304 of the first region and at least partially along the center line (L1). Similar to the tab 13 as illustrated in FIG. 1, the sheet-formed tab 313 as shown in FIGS. 3 and 4 extends in a longitudinal direction from an edge portion 304 and has an extension (A) along the center line (L1) from a tab base (B) to an outer edge 318 of the tab 313. The tab base (B) is a transversal line (B) that longitudinally divides the tab 313 with adhesive-free surfaces 316, 317 from the transverse edge portion 304 carrying resealable adhesive 12 in the first region 310, to which resealable adhesive 12 the tab 313 base (B) has a point of contact. The point of contact is at an edge of the resealable adhesive 12 that provides the shortest extension (A).

In order to obtain a tight package, the transverse edge portion 304 of the packaging unit 301 is provided with resealable adhesive 12. Folding then ensures that the first region 310 comprising the adhesive-covered transverse edge portion 304 forms a lid, and the resealable adhesive positioned at the transverse edge portion 304 seals the packaging unit 301, with the sheet-formed tab 313 extending from the lid. It is also conceivable to provide each one of the opposite transverse edges with resealable adhesive.

Thus, also in the packaging unit with two folding axes, the tab portion may extend from an edge 319 of the folded packaging unit to provide a free-end and material overhang that is adhesive free and easy to grip by a user's hand as compared to known adhesive-free end portions and tabs. The sheet-formed tab portion 13 does not overlap with any other packing unit regions 310-312. The longitudinal tab extension (overhang) from the edge 319 of the folded packaging unit 301 to an outer edge 318 of the tab 313 may be any shape and extension according to the present disclosure and as defined by the appended claims, e.g. the shapes and dimensions as described for the single-axis packaging unit.

It should be noted that when the packaging unit according to the present disclosure is used for disposal, the user can choose to roll up the packaging unit 1, 301 and the soiled article positioned on it rather than folding it. This rolling action is made easier by the provision of a finger-gripping tab 13, 313. If the gripping tab 13, 313 is used in such rolling action, the skilled person can choose to roll the packaging unit 1, 301 such that the tab is part of an outermost layer of the rolled packaging unit.

The illustrated packaging units 1, 301 may be formed from a sheet of material having a longitudinal direction (L) and a transverse direction (T). The method comprises the steps of: a) providing the sheet of material, the sheet having an inner surface 2, 302 and an outer surface 3, 303, the inner surface 2,302 comprising an edge zone, and b) providing an edge portion 4', 6, 8; 304, 306, 305', 307 of the edge zone with resealable adhesive 12, e.g. in a chessboard pattern as shown in FIGS. 1-4.

The method may further comprise the step of folding the sheet along the at least one folding axis 9; 309, 309' with the first and second regions 10, 11; 311, 312 in an overlapping configuration, thereby providing a packaging unit 1, 301 of overlapping sheet layers as described herein above. In such a folded packaging unit 1, 301, the tab 13, 313 may form an overhang as described hereinabove.

As the skilled person will appreciate, it is intended that the detailed description be regarded as illustrative and that many embodiments and alternatives are possible within the scope of the present disclosure as defined by the appended claims. For example, the packaging unit may adopt other geometrical shapes than the rectangular ones shown in the drawings. The geometrical shape of the sheet can vary depending on the type of the hygiene article to be packaged. The sheet may be circular, triangular, square, rectangular, or any other shape suitable for the hygiene article to be packaged. It is desirable, however, that the sheet has at least one symmetry axis.

Furthermore, the present disclosure has been exemplified with packaging units comprising resealable adhesive for closure of the packaging unit, wherein a chessboard pattern of resealable adhesive and non-adhesive portions is formed along at least longitudinal edge zones (i.e. along the longitudinal direction (L)) for complementary attachment between resealable adhesive and non-adhesive portions in a folded packaging unit. Other ways of applying one or more resealable adhesive portions for closure of the packaging unit may also be considered.

The invention claimed is:

1. A packaging unit for hygiene articles, the packaging unit being formed from a sheet of material comprising:
 a longitudinal direction and a transverse direction,
 said sheet having an inner surface and an outer surface,
 said inner surface comprising an edge zone that comprises an edge portion being provided with a resealable adhesive for closure of the packaging unit,
 said sheet having a longitudinal center line and at least one transversely extending folding axis,
 said folding axis dividing a first region of the sheet from a second region of the sheet,
 a portion of the sheet forms a single tab extending from the edge portion of the first region and at least partially along the center line,
 the single tab having two major surfaces being free of any adhesive for closure of the packaging unit, wherein the single tab extends in the longitudinal direction from said edge portion of the first region so that the single tab extends along or parallel to the center line from a tab base at said edge portion of the first region to an outer edge of the single tab at least 0.5 cm,
 said tab base being a transversal line that longitudinally divides the single tab with adhesive-free surfaces from a portion of the first region containing said resealable adhesive for closure of the packaging unit, to which resealable adhesive the tab base has a point of contact,
 wherein the outer surface of the first region forms an outer layer of the folded packaging unit, and
 wherein said sheet is folded along said at least one transversely extending folding axis such that said first region overlaps said second region, thereby providing a packaging unit of overlapping sheet layers, and the single tab protrudes outwardly from an edge defined by the overlapping sheet layers of the folded packaging unit such that the single tab does not overlap with any other portion of the packaging unit,
wherein:
 the first region includes an inner edge portion and an outer edge portion of a first edge zone of said first region that is provided with a first resealable adhesive, such that the other of said inner edge portion and said outer edge portion of said first edge zone of said first region is adhesive-free; and the second region includes an inner edge portion and an outer edge portion of a first edge zone of said second region with a first resealable adhesive, such that the other of said inner edge portion and said outer edge portion of said edge zone of said second region is adhesive-free in a complementary manner to said first edge zone of said first region.

2. A packaging unit according to claim 1, wherein said sheet is of substantially rectangular shape and comprises longitudinal edges and transverse edge portions, wherein the single tab is arranged at one of the transverse edge portions.

3. The packaging unit according to claim 2, wherein said sheet has two folding axes, dividing said sheet into said first region, said second region and a third region.

4. The packaging unit according to claim 3, wherein said sheet is folded along said two folding axes with said first region, said second and said third region in an overlapping configuration of three layers.

5. Packaging unit according to claim 1, wherein a transverse edge portion of the sheet comprises the resealable adhesive for closure of the packaging unit to which the tab base is in contact.

6. The packaging unit according to claim 1, wherein a maximum extension of the single tab from the tab base is substantially along the center line.

7. The packaging unit according to claim 1, wherein the single tab is tongue-shaped, and a tip of the tongue shape is arranged close to, or at, the center line.

8. The packaging unit according to claim 1, wherein the sheet is a single-ply material.

9. The packaging unit according to claim 8, wherein the single-ply material is of polyolefin.

10. The packaging unit according to claim 1, wherein the single tab is integrally formed with the sheet.

11. The packaging unit according to claim 1, wherein at least one of said sheet and said single tab are at least one of:
opaque; and
at least one of comprising print and tactile indications.

12. The packaging unit according to claim 11, wherein the single tab is embossed.

13. The packaging unit according to claim 1, wherein said resealable adhesive is a pressure-sensitive hotmelt adhesive.

14. The packaging unit according to claim 1, wherein said packaging unit is reclosable.

15. A method of forming a packaging unit for hygiene articles, the packaging unit being formed from a sheet of material having a longitudinal direction and a transverse direction, the method comprising the steps of:
providing said sheet of material, the sheet of material having an inner surface and an outer surface, said inner surface comprising an edge zone,
providing an edge portion of said edge zone with resealable adhesive;
wherein said sheet of material has a longitudinal center line and at least one transversely extending folding axis, said folding axis dividing a first region of the sheet of material from a second region of the sheet of material;
wherein a portion of the sheet forms a single tab at an edge portion of the first region and at least partially along the center line, the single tab having two major surfaces being free of any adhesive for closure of the packaging unit,
wherein the single tab extends in the longitudinal direction from said edge portion of the first region so that the single tab extends along or parallel to the center line from a tab base at said edge portion of the first region to an outer edge of the single tab at least 0.5 cm,
said tab base being a transversal line that longitudinally divides the single tab with adhesive-free surfaces from a portion of the first region containing said resealable adhesive for closure of the packaging unit, to which resealable adhesive the tab base has a point of contact,
wherein the method further comprises the step of:
folding said sheet along said at least one folding axis such that said first region overlaps with said second region, thereby providing a packaging unit of overlapping sheet layers,
wherein an outer surface of the first region forms an outer layer of the folded packaging unit, and the single tab protrudes outwardly from an edge defined by the overlapping sheet layers of the folded packaging unit such that the single tab does not overlap with any other portion of the packaging unit,
wherein:
the first region includes an inner edge portion and an outer edge portion of a first edge zone of said first region that is provided with a first resealable adhesive, such that the other of said inner edge portion and said outer edge portion of said first edge zone of said first region is adhesive-free; and
the second region includes an inner edge portion and an outer edge portion of a first edge zone of said second region with a first resealable adhesive, such that the other of said inner edge portion and said outer edge portion of said edge zone of said second region is adhesive-free in a complementary manner to said first edge zone of said first region.

16. A packaging unit for hygiene articles, the packaging unit being formed from a sheet of material comprising:
a longitudinal direction and a transverse direction,
said sheet having an inner surface and an outer surface,
said inner surface comprising an edge zone that comprises an edge portion being provided with a resealable adhesive for closure of the packaging unit,
said sheet having a longitudinal center line and at least one transversely extending folding axis,
said folding axis dividing a first region of the sheet from a second region of the sheet,
wherein a single tab is arranged at an edge portion of the first region and at least partially along the center line,
the single tab being free of any adhesive, wherein the single tab extends in the longitudinal direction from said edge portion of the first region so that the single tab extends along or parallel to the center line from a tab base at said edge portion of the first region to an outer edge of the single tab at least 0.5 cm,
said tab base being a transversal line that longitudinally divides the adhesive-free tab from a portion of the first region containing said resealable adhesive for closure of the packaging unit, to which resealable adhesive the tab base has a point of contact,
wherein the outer surface of the first region forms an outer layer of the folded packaging unit, and
wherein said sheet is folded along said at least one transversely extending folding axis such that said first region overlaps said second region, thereby providing a packaging unit of overlapping sheet layers, and the single tab protrudes outwardly from the overlapping sheet layers of the folded packaging unit such that the single tab does not overlap with any other portion of the packaging unit,
wherein:

the first region includes an inner edge portion and an outer edge portion of a first edge zone of said first region that is provided with a first resealable adhesive, such that the other of said inner edge portion and said outer edge portion of said first edge zone of said first region is adhesive-free; and the second region includes an inner edge portion and an outer edge portion of a first edge zone of said second region with a first resealable adhesive, such that the other of said inner edge portion and said outer edge portion of said edge zone of said second region is adhesive-free in a complementary manner to said first edge zone of said first region.

\* \* \* \* \*